(12) United States Patent
Venkatesh et al.

(10) Patent No.: US 8,137,734 B2
(45) Date of Patent: Mar. 20, 2012

(54) PREPARATION OF CONTROLLED RELEASE SKELETAL MUSCLE RELAXANT DOSAGE FORMS

(75) Inventors: Gopi M. Venkatesh, Vandalia, OH (US); James M. Clevenger, Vandalia, OH (US); Timothy Grinstead, Beavercreek, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 30 days.

(21) Appl. No.: 12/487,339

(22) Filed: Jun. 18, 2009

(65) Prior Publication Data

US 2010/0098832 A1  Apr. 22, 2010

Related U.S. Application Data

(60) Provisional application No. 61/074,464, filed on Jun. 20, 2008.

(51) Int. Cl.
  *A61K 9/28* (2006.01)
(52) U.S. Cl. ....... 427/2.14; 424/269; 424/472; 424/469; 424/489; 424/464; 424/468; 424/471; 424/482; 424/484; 34/27; 427/2.15; 427/2.16; 427/402; 427/414
(58) Field of Classification Search ...... 34/27; 424/472, 424/469; 427/2.14, 2.15, 2.16
See application file for complete search history.

(56) References Cited

U.S. PATENT DOCUMENTS

| | | | |
|---|---|---|---|
| 3,882,246 A | 5/1975 | Share | |
| 4,337,582 A * | 7/1982 | Smith | ............................. 34/469 |
| 4,685,918 A | 8/1987 | Amidon et al. | |
| 5,047,258 A | 9/1991 | Belanger et al. | |
| 7,387,793 B2 | 6/2008 | Venkatesh et al. | |
| 7,544,372 B2 | 6/2009 | Venkatesh et al. | |
| 7,790,199 B2 | 9/2010 | Venkatesh et al. | |
| 7,820,203 B2 | 10/2010 | Venkatesh et al. | |
| 7,829,121 B2 | 11/2010 | Venkatesh et al. | |
| 2005/0106247 A1* | 5/2005 | Venkatesh et al. ............ 424/469 |
| 2006/0039975 A1 | 2/2006 | Vilkov et al. | |
| 2006/0165795 A1* | 7/2006 | Sawicka | ........................ 424/472 |
| 2006/0263429 A1* | 11/2006 | Feng | ............... 424/469 |
| 2007/0184112 A1 | 8/2007 | Wong et al. | |
| 2007/0244093 A1 | 10/2007 | Boehm et al. | |
| 2009/0148532 A1 | 6/2009 | Venkatesh et al. | |

FOREIGN PATENT DOCUMENTS

| | | |
|---|---|---|
| WO | WO 01/19901 | 3/2001 |
| WO | WO 02/08327 | 1/2002 |
| WO | WO 2005/048996 | 6/2005 |
| WO | WO 2009/155426 | 12/2009 |

OTHER PUBLICATIONS

Examination Report Issued on Feb. 26, 2010, in connection with Panama Patent Appl. No. 88323.
International Search Report based on International Application No. PCT/US2009/047807 (Aug. 6, 2009).
Written Opinion of the International Searching Authority based on International Application No. PCT/US2009/047807 (Aug. 6, 2009).

* cited by examiner

*Primary Examiner* — Dah-Wei Yuan
*Assistant Examiner* — Andrew Bowman
(74) *Attorney, Agent, or Firm* — Cooley LLP

(57) ABSTRACT

The present invention is directed to a method of preparing an extended release pharmaceutical composition comprising cyclobenzaprine, comprising coating inert particles with a cyclobenzaprine-containing a drug layering composition to form IR beads, then coating the IR beads with an extended-release coating to form ER beads.

28 Claims, 4 Drawing Sheets

PREPARATION OF CONTROLLED RELEASE SKELETAL MUSCLE RELAXANT DOSAGE FORMS

CROSS-REFERENCE TO RELATED APPLICATIONS

This application claims priority to U.S. Provisional Application Ser. No. 61/074,464, filed Jun. 20, 2008, the disclosure of which is herein incorporated by reference in its entirety for all purposes.

BACKGROUND OF THE INVENTION

A major objective of developing and commercializing controlled release dosage forms for indications such as cardiovascular diseases, chronic pain, relief of muscle spasm and associated symptoms especially in the elderly is to deliver the drug so as to maintain the drug at therapeutically effective concentrations over an extended period of time, thereby enhancing patient compliance and therapeutic efficacy, thereby reducing both cost of treatment and side effects.

Many therapeutic agents are most effective when made available at a constant rate at or near the absorption site. The absorption of therapeutic agents thus made available generally results in desired plasma concentrations leading to maximum efficacy and minimum toxic side effects. Much effort has been devoted to developing matrix tablet based and multiparticulate capsule based drug delivery systems for oral applications.

U.S. Pat. No. 4,839,177 to Colombo, et al, assigned to Jagotec AG, refers broadly to controlled release of active substances including medicaments and any type of substance which is to be released at a controlled rate into an aqueous fluid. The patent is directed to a system for the controlled-rate release of active substances consisting of a deposit core comprising an active substance and at least one of (a) a polymeric material having a high degree of swelling on contact with water and a gellable polymeric material or (b) a single polymeric material having both swelling and gelling properties, and a support platform applied to the deposit core wherein the support platform consists of a water insoluble polymeric material.

U.S. Pat. Nos. 4,851,228 and 4,968,507, both to Zentner et al., assigned to Merck & Company, refer to a multi-particulate osmotic pump for the controlled release of a pharmaceutically active agent, each osmotic pump element consisting essentially of a core containing an active agent and a rate controlling water insoluble wall comprising a semi-permeable polymer and at least one pH insensitive pore forming additive dispersed throughout the wall. U.S. Pat. No. 4,590,062 to Jang assigned to Tech Trade Corporation and U.S. Pat. No. 4,882,167 to Jang, are directed to a compressed product containing an active produced by dry blending with a matrix combination of a hydrophobic polymer (e.g. ethylcellulose) and a wax, fatty acid, neutral lipid or combination thereof.

U.S. Pat. No. 4,996,047 to Kelleher, assigned to Richardson-Vicks, is directed to an oral pharmaceutical composition in unit dosage form of ion-exchange resin particles having a pharmacologically active drug bound thereto wherein the drug-resin complex particles have been coated with a water-impermeable diffusion barrier to provide controlled release of the active drug. U.S. Pat. No. 5,120,548 to McClelland et al., assigned to Merck & Company, is directed to a controlled release drug delivery device comprising a composition of a polymer which swells upon exposure to an aqueous environment, a plurality of controlled release swelling modulators, at least one active agent and either a water insoluble polymer coating surrounding the composition or a microporous wall surrounding the composition. U.S. Pat. No. 5,350,584 to McClelland et al., assigned to Merck & Company, relates to a process for the production of microcrystalline cellulose-free multiparticulates comprising a medicament and a charged resin. The resulting spheronized beads can be used in certain controlled release dosage forms.

U.S. Pat. No. 5,366,738 to Rork et al., assigned to Merck & Company, is directed to a drug delivery device for controlled release of an active agent. The drug delivery device includes a compressed core with an active agent and a polymer which forms gelatinous microscopic particles upon hydration and a water insoluble, water impermeable polymeric coating comprising a polymer and plasticizer which surrounds and adheres to the core.

U.S. Pat. No. 5,582,838 to Rork et al., assigned to Merck & Company, is related to a drug delivery device for the controlled release of a beneficial agent. The drug delivery device includes a compressed core having at least two layers: at least one layer is a mixture of a beneficial agent and a polymer which forms microscopic polymer gel beads upon hydration and at least one outer layer comprises a polymer which forms microscopic polymer gel beads upon hydration. A water insoluble, water impermeable coating is applied to the core and the coating has apertures exposing between about 5-75% of the core surface.

U.S. Pat. No. 5,874,418 to Stella et al., assigned to Cydex, is directed to a pharmaceutical composition comprising a carrier and a mixture of a sulfoalkyl ether-cyclodextrin and a therapeutic agent wherein a major portion of the therapeutic agent is not complexed to the sulfoalkyl ether-cyclodextrin derivative. Delayed, sustained or controlled release formulations are also described wherein the pharmaceutical core is coated with a film coating comprising a file forming agent and a pore forming agent. U.S. Pat. No. 5,882,682 to Rork et al., assigned to Merck & Company, is directed to a drug delivery process including the steps of preparing a uniform mixture of a polymer which forms gelatinous microscopic particles upon hydration, the beneficial agent and other excipients used in the preparation of the core; compressing the mixture into cores; coating the entire core with a water insoluble, water impermeable polymeric coating including a polymer and a plasticizer; and forming apertures through the coating.

U.S. Pat. No. 5,952,451 to Zhao, assigned to Guilford Pharmaceuticals is directed to a process for preparing high molecular weight poly(phosphoester) compositions comprising a biologically active substance and a poly(phosphoester) and the high molecular weight compositions produced thereby. The polymers so produced are useful in prolonged released drug delivery systems. U.S. Pat. No. 6,004,582 to Faour et al., assigned to Laboratorios Phoenix U.S.A., is directed to a multi-layered osmotic device comprising a compressed core including a first active agent and an osmotic agent, a semi-permeable membrane surrounding the core and having a preformed passageway therein wherein the membrane is permeable to a fluid in the environment of use and substantially impermeable to the first active agent. The semi-permeable membrane preferably consists essentially of cellulose acetate and poly(ethylene glycol). The external coat can include poly(vinylpyrrolidone) and poly(ethylene glycol) and can further includes materials such as HPMC, ethylcellulose, hydroxyl ethylcellulose, CMC, dimethylaminoethyl methacrylate-methacrylic acid ester copolymer, ethyl acrylate-methyl methacrylate copolymer, and combinations thereof.

WO 99/18937 to Kleinbart et al., (Merck & Company), is directed to a composition comprising a pharmaceutically effective amount of cyclobenzaprine and calcium phosphate dibasic hydrous, wherein the tablet releases most of the active component within an hour. WO 99/30671 to Ron E. S., is directed to an oral delivery vehicle including an aspected particle comprising a pharmaceutically active component and excipients wherein the vehicle is formulated to provide controlled delivery of the pharmaceutically active component. The vehicle may further contain a coating to provide sustained drug delivery to the particle. WO 98/53802 to Faour et al., (Laboratorios Phoenix USA), is directed to a multi-layered osmotic device that is capable of delivering a first active agent in an outer lamina to one environment of use and a second active agent in the core to another environment of use. An erodible polymer coat between an internal semipermeable membrane and a second active agent-containing external coat comprises poly(vinylpyrrolidone)-vinyl acetate) copolymer. The active agent in the core is delivered through a pore containing an erodible plug.

WO 98/18610 to Van Lengerich, is directed to particles containing an active agent, which provide controlled release of the active ingredient without substantial destruction of the matrix material. A release-rate controlling component is incorporated in a matrix to control the rate-release of the encapsulant from the particles. A hydrophobic component or a high water binding capacity component may be used for extending the release time. Release properties may also be controlled by precoating the encapsulant and/or coating the particles with a film-forming component. WO 98/06439 to Oedemoed, (Osteotech), is directed to a composition comprising a biologically active agent encapsulated in a matrix comprising a polyether ester copolymer, such as polyethylene glycol terephthalate/polybutylene-terephthalate copolymer. The polyether ester copolymer protects the active agent from degradation and thereby facilitates the drug delivery.

Cyclobenzaprine hydrochloride, a skeletal muscle relaxant, is a centrally acting drug which reduces or abolishes excessive tonic muscle activity in hypertonic as opposed to hyperphasic disorders. Flexeril® is an immediate release cyclobenzaprine composition in the form of a coated tablet. Flexeril® tablets are prepared by mixing and compressing the cyclobenzaprine and excipients (lactose, starch, magnesium stearate, and coloring agents), then coating the resulting tablet with a water-soluble, pharmaceutically acceptable polymer solution (hydroxypropylcellulose/hydroxypropylmethylcellulose). Flexeril® tablets are available in either 5 mg or 10 mg dosages, and are typically administered three times a day to produce the desired therapeutic effect. Flexeril® IR (immediate release) tablets containing 10 mg of cyclobenzaprine HCl are administered three times a day to relieve skeletal muscle spasm of local origin without interfering with muscle function. The oral administration thrice daily is an issue of patient compliance, especially with the elderly. Hence, there is a need for modified release skeletal muscle relaxant suitable for a single daily administration, particularly in 15 mg and 30 mg dosage forms, to substantially minimize intersubject variability and improve the quality of life, especially in the elderly population.

In addition, it is important to have a manufacturing process that reproducibly and consistently produces pharmaceutical dosage forms delivering specified pharmacokinetic properties and performing under real-world transport and storage conditions. A process that fails to consistently deliver product meeting approved specifications is not practical for commercial purposes. Out-of-specification products must be discarded because they are not guaranteed to deliver the pharmacokinetic and stability performance approved by regulatory agencies. Manufacturing processes typically involve numerous steps, any one of which could affect the pharmacokinetic performance properties of the resulting product.

SUMMARY OF THE INVENTION

In one embodiment, the present invention relates to a method of preparing a pharmaceutical composition comprising: a) preparing immediate release (IR) beads comprising cyclobenzaprine or a pharmaceutically acceptable salt, solvate, and/or ester thereof; and b) coating the IR beads with an ER coating composition comprising a pharmaceutically acceptable water-insoluble polymer, under an atmosphere having a dew point ranging from about 5-20° C., thereby forming ER beads. In another embodiment, the method further comprises coating the IR beads of step a) with a seal-coating composition comprising a pharmaceutically acceptable water-soluble polymer before said ER coating step b).

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; and b) coating the IR beads with an ER coating composition comprising a pharmaceutically acceptable water-insoluble polymer, under an atmosphere having a dew point ranging from about 5-20° C., thereby forming ER beads. In another embodiment, the method further comprises coating the IR beads of step a) with a seal-coating composition comprising a pharmaceutically acceptable water-soluble polymer before said ER coating step b).

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; b) coating the drug layered beads with a seal-coating composition comprising a pharmaceutically acceptable water soluble polymer, thereby forming IR beads; and c) coating the IR beads with an ER coating composition comprising a pharmaceutically acceptable water-insoluble polymer, under an atmosphere having a dew point ranging from about 5-20° C., thereby forming ER beads.

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; b) coating the IR beads with an ER coating composition comprising a pharmaceutically acceptable water-insoluble polymer, under an atmosphere having a dew point ranging from about 5-20° C., thereby forming ER beads; and c) curing the ER beads at about 60° C. for about 4-12 hours under an atmosphere having a dew point ranging from about 5-20° C.

In one embodiment, the present invention relates to a method of preparing a pharmaceutical composition comprising: coating about 20-25 mesh inert particles with a drug layering composition comprising cyclobenzaprine or a pharmaceutically acceptable salt, solvate, and/or ester thereof, and a pharmaceutically acceptable solvent, e.g., an aqueous organic solvent; drying the coated inert particles, thereby forming drug layered beads; coating the drug layered beads with a seal coating composition comprising a pharmaceutically acceptable water soluble polymer and water; drying the coated drug layered beads, thereby forming IR beads; and coating the IR beads with an ER coating composition comprising a pharmaceutically acceptable water-insoluble polymer, under an atmosphere having a dew point ranging from about 5-20° C., thereby forming ER beads. In another embodiment, the present method is directed to a method of preparing a pharmaceutical composition comprising coating about 20-25 mesh inert particles with an about 25 wt. % solids content drug layering composition comprising cyclobenzaprine or pharmaceutically acceptable salts, solvates, and/or esters thereof, and an aqueous organic solvent; drying the coated inert particles, thereby forming drug layered beads; coating the drug layered beads with an about 8-10 wt. % solids content seal coating composition comprising a pharmaceutically acceptable water soluble polymer and water; drying the coated drug layered beads, thereby forming IR beads (e.g., drug load: 25% w/w); coating the IR beads with an about 6 wt. % solids content ER coating composition comprising a pharmaceutically acceptable water-insoluble polymer and an optional plasticizer; drying the coated IR beads under an atmosphere having a dew point ranging from about 5-20° C., thereby forming ER beads; and optionally curing the sieved ER beads at about 60° C. for up to about 4 hours, under an atmosphere having a dew point ranging from about 5-20° C.

BRIEF DESCRIPTION OF THE DRAWINGS

The invention will be described in further detail with reference to the accompanying Figures wherein.

DETAILED DESCRIPTION OF THE INVENTION

Figure 1:
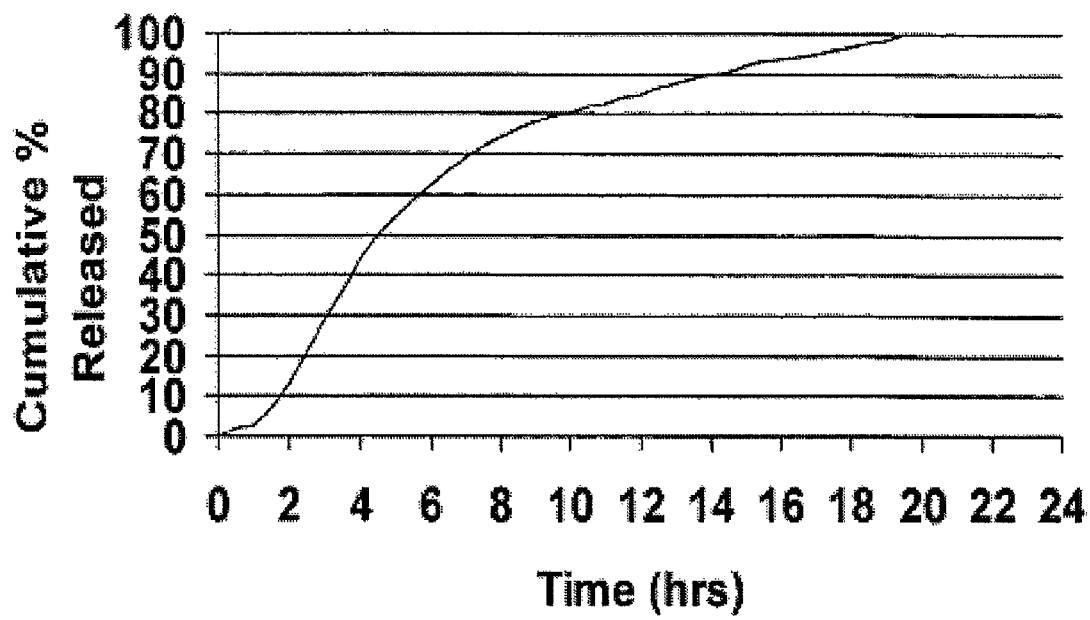
FIG. 1 shows the proposed target release profile for cyclobenzaprine hydrochloride MR (modified release) capsules.

All documents cited herein are incorporated by reference in their entirety for all purposes. The citation of any document is not to be construed as an admission that it is prior art with respect to the present invention.

The terms "drug", "active", "active pharmaceutical ingredient", etc. are used interchangeably.

All references to a particular drug or active herein include pharmaceutically acceptable salts, solvates, esters, isomers, etc. thereof unless expressly indicated otherwise.

In its various embodiments, the present invention is directed to methods of preparing pharmaceutical compositions as described herein, i.e., methods for preparing oral dosage forms of skeletal muscle relaxants, for example cyclobenzaprine.

In one embodiment, the present invention relates to a method of preparing a pharmaceutical composition comprising: a) preparing immediate release (IR) beads comprising cyclobenzaprine or a pharmaceutically acceptable salt, solvate, and/or ester thereof; and b) coating the IR beads with an ER coating composition comprising a pharmaceutically acceptable water-insoluble polymer, under an atmosphere having a dew point ranging from about 5-20° C., thereby forming ER beads. In another embodiment, the method further comprises coating the IR beads of step a) with a seal-coating composition comprising a pharmaceutically acceptable water-soluble polymer before said ER coating step b).

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; and b) coating the IR beads with an ER coating composition comprising a pharmaceutically acceptable water-insoluble polymer, under an atmosphere having a dew point ranging from about 5-20° C., thereby forming ER beads. In another embodiment, the method further comprises coating the IR beads of step a) with a seal-coating composition comprising a pharmaceutically acceptable water-soluble polymer before said ER coating step b).

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; b) coating the drug layered beads with a seal-coating composition comprising a pharmaceutically acceptable water soluble polymer, thereby forming IR beads; and c) coating the IR beads with an ER coating composition comprising a pharmaceutically acceptable water-insoluble polymer, under an atmosphere having a dew point ranging from about 5-20° C., thereby forming ER beads. In one embodiment, the inert particles have a particle size of about 20-25 mesh. In another embodiment the pharmaceutically acceptable solvent in the drug-layering composition comprises an aqueous organic solvent. In another embodiment, the seal-coating composition further comprises water as a solvent.

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; b) coating the IR beads with an ER coating composition comprising a pharmaceutically acceptable water-insoluble polymer, under an atmosphere having a dew point ranging from about 5-20° C., thereby forming ER beads; and c) curing the ER beads at about 60° C. for about 4-12 hours under an atmosphere having a dew point ranging from about 5-20° C.

In one embodiment, the present invention relates to a method of preparing a pharmaceutical composition comprising: a) coating inert particles with a drug-layering composition comprising cyclobenzaprine or a pharmaceutically acceptable salt, solvate, and/or ester thereof, and a pharmaceutically acceptable solvent, thereby forming drug layered beads; b) coating the drug layered beads with a seal-coating composition comprising a pharmaceutically acceptable water soluble polymer, thereby forming IR beads; and c) coating the IR beads with an ER coating composition comprising a pharmaceutically acceptable water-insoluble polymer, under an atmosphere having a dew point ranging from about 5-20° C., thereby forming ER beads. In yet another embodiment, the present invention further comprises curing the ER beads from step c), above at about 60° C. under an atmosphere having a dew point ranging from about 5-20° C. The curing process may be carried out for about 12 hours, about 10 hours, about 8 hours, about 6 hours, about 4 hours, or about 2 hours.

In another embodiment, the present invention further comprises a drying step after forming the drug-layered beads. For example, the method comprises preparing a pharmaceutical composition comprising: (a) coating inert particles with a drug-layering composition comprising cyclobenzaprine or a pharmaceutically acceptable salt, solvate, and/or ester thereof, and a pharmaceutically acceptable solvent, thereby forming drug-layered beads; (a1) drying the drug-layered beads; (b) coating the drug-layered beads with a seal-coating composition comprising a pharmaceutically acceptable water-soluble polymer, thereby forming IR beads; and (c) coating the IR beads with an ER coating composition comprising a pharmaceutically acceptable water-insoluble polymer, under an atmosphere having a dew point ranging from about 5-20° C., thereby forming ER beads. In another embodiment, the drying step (a1) is carried out under an atmosphere having a dew point ranging from about 5-20° C.

In another embodiment, the present invention further comprises a drying step after forming the IR beads. For example, the method comprises preparing a pharmaceutical composition comprising: (a) coating inert particles with a drug-layering composition comprising cyclobenzaprine or a pharmaceutically acceptable salt, solvate, and/or ester thereof, and a pharmaceutically acceptable solvent, thereby forming drug-layered beads; (b) coating the drug-layered beads with a seal-coating composition comprising a pharmaceutically acceptable water-soluble polymer, thereby forming IR beads; (b1) drying the IR beads; and (c) coating the IR beads with an ER coating composition comprising a pharmaceutically acceptable water-insoluble polymer, under an atmosphere having a dew point ranging from about 5-20° C., thereby forming ER beads. In another embodiment, the drying step (b1) is carried out under an atmosphere having a dew point ranging from about 5-20° C.

In another embodiment, the present invention further comprises a drying step after forming the ER beads. For example, the method comprises preparing a pharmaceutical composition comprising: (a) coating inert particles with a drug-layering composition comprising cyclobenzaprine or a pharmaceutically acceptable salt, solvate, and/or ester thereof, and a pharmaceutically acceptable solvent, thereby forming drug-layered beads; (b) coating the drug-layered beads with a seal coating composition comprising a pharmaceutically acceptable water-soluble polymer, thereby forming IR beads; and (c) coating the IR beads with an ER coating composition comprising a pharmaceutically acceptable water-insoluble polymer, under an atmosphere having a dew point ranging from about 5-20° C.; (c1) drying the coated immediate release beads, thereby forming ER beads.

In one embodiment, the present invention relates to a method of preparing a pharmaceutical composition comprising: (a) coating about 20-25 mesh inert particles with a drug layering composition comprising cyclobenzaprine or a pharmaceutically acceptable salt, solvate, and/or ester thereof, and an aqueous organic solvent; b) drying the coated inert particles, thereby forming drug layered beads; c) coating the drug layered beads with a seal coating composition comprising a pharmaceutically acceptable water soluble polymer and water; d) drying the coated drug layered beads, thereby forming IR beads; e) coating the IR beads with an ER coating composition comprising a pharmaceutically acceptable water-insoluble polymer; f) drying the coated immediate release beads under an atmosphere having a dew point ranging from about 5-20° C., thereby forming ER beads.

In one embodiment, pharmaceutically acceptable inert particles are first coated with a drug layering composition. Non-limiting examples of suitable pharmaceutically acceptable particles include sugar spheres or beads (e.g., Celphere®), cellulose spheres, silicon dioxide spheres, acidic buffer particles, alkaline buffer particles, or the like, having a suitable particle size or particle size distribution, e.g., about 20-25 mesh. In one embodiment, the inert particles are sugar beads (non-pareil seeds) having a particle size of about 20-25 mesh. In another embodiment, the drug-containing particles may be prepared by granulating and milling, by controlled spheroinization in Granurex 40, or by granulation and extrusion/spheroinization to form IR pellets.

The drug layering composition comprises the drug (e.g., cyclobenzaprine and pharmaceutically acceptable salts, solvates, and/or esters thereof) dissolved or dispersed in an aqueous organic solvent. Non-limiting aqueous organic solvents include aqueous ketones or aqueous alcohols, for example aqueous acetone. In one embodiment, the aqueous organic solvent is 1:1 water/acetone, and the drug is cyclobenzaprine hydrochloride, e.g., dissolved to a solids content of about 25 wt. %.

In other embodiments, the drug layering composition further comprises an optional binder, for example a pharmaceutically acceptable water soluble polymer such as polyvinylpyrrolidone (PVP), carboxyalkylcelluloses, polyethylene oxide, polysaccharides such as dextran, corn starch, cellulose derivatives such as hydroxypropyl methylcellulose (HPMC) and hydroxypropylcellulose. In one embodiment, the drug layering composition contains a binder as described herein. In another embodiment, the drug layering composition does not contain a binder.

The coating weight of the drug layering composition (i.e., the weight of the solids dissolved in the aqueous organic solvent deposited on the inert particles, expressed as a percentage weight increase of the beads after coating and drying) can vary depending on the desired dosage of the drug, and can range from about 5 wt. % to about 30 wt. %, including about 5 wt. %, about 10 wt. %, about 15 wt. %, about 20 wt. %, about 25 wt. %, or about 30 wt. %. In one embodiment, the coating weight of the drug layering composition is about 25 wt. %.

The drug layering composition can be applied by any suitable method, including a continuous or batch type fluid bed coating apparatus such as those manufactured by Glatt. For example, the drug layering can be carried out on a Glatt GPCC 120 equipped with an 18 inch bottom spray Wurster insert (e.g., using a type "C" air distribution plate with 1.5 mm holes at the center and 2.0 mm holes that the outer circumference, or a type "D" air distribution plate with 2.0 mm holes at the center and 3.5 mm holes at the outer circumference). The fluid bed coating apparatus can be operated under any suitable conditions which minimize agglomeration of the drug layered beads during coating, and which provide the coating weight described herein. For example, the partition height from the distribution plate can be about 53 mm, ranging from about 45 mm to about 55 mm. In one embodiment, the partition height from the distribution plate is about 53±2 mm. Likewise, the rate at which the drug layering composition is sprayed onto the inert particles and the process air volume (and other operating parameters) can be modified, e.g. to obtain the desired coating weight. For example, in one embodiment the spray rate ranges from 100 g/min to about 400 g/min, and the process air volume ranges from about 800-1500 CFM.

In one embodiment, the dried drug layered beads can then be coated with a seal coating composition, for example to improve the mechanical strength of the drug layered beads. Any suitable seal coating composition can be used which does not interfere with the properties of the extended release coating added in subsequent steps. Suitable seal coating compositions comprise a pharmaceutically acceptable water-soluble polymer dissolved or dispersed in water. Non-limiting examples of water-soluble polymers include polyethylene glycol, hydroxypopylmethylcellulose, hydroxypropylcellulose, hydroxyethylcellulose, methylcellulose, polyvinylpyrrolidone and mixtures thereof. In one embodiment, the water-soluble polymer is hydroxypropylmethylcellulose (e.g., Opadry® Clear). The solids content of the seal coating composition can range from about 2 wt. % to about 10 wt. %, for example about 2 wt. %, about 3 wt. %, about 4 wt. %, about 5 wt. %, about 6 wt. %, about 7 wt. %, about 8 wt. %, about 9 wt. %, or about 10 wt. %. In one embodiment, the solids content of the seal coating composition is about 8-10 wt. %. In another embodiment, the solids content of the seal coating composition is about 8 wt. %.

In one embodiment, the seal coating step can be carried out, for example, using a fluid bed coating apparatus as described herein, and can be dried under suitable conditions, for example in a fluid bed coating apparatus under temperature conditions as described herein. For example, the seal coating composition can be applied to a spray rate of about 200 g/min, and dried at a product temperature ranging from about 35° C. to about 60° C. In one embodiment, the product temperature is about 42° C. The resulting seal coated drug layered beads are then referred to as "immediate release" (IR) beads because the drug is released essentially immediately upon dissolution or administration.

After layering with the drug layering composition, the resulting drug layered beads are dried to remove the aqueous organic solvent. Any suitable drying conditions can be used which do not degrade the drug (e.g. cyclobenzaprine or its pharmaceutically acceptable salts, solvates, and/or esters). For example, the drug layered beads can be dried in the coating apparatus (e.g., a fluid bed coating apparatus such as a Glatt fluid bed coater equipped with a Wurster insert). Suitable drying temperatures are approximately 50° C., for example in the range of about 45° C. to about 55° C.

If desired, after drying the IR beads can optionally be "sized" to remove fines (i.e., very fine particles) or agglomerates. For example the IR beads can be "sieved" with 14-mesh and 24-mesh screens to remove undersized and oversized particles.

The IR beads are then coated with an "extended release" (ER) coating composition comprising a pharmaceutically acceptable water insoluble polymer. Non-limiting examples of suitable pharmaceutically acceptable water-insoluble polymers include waxes, water-insoluble cellulose derivatives (e.g. ethylcellulose, ethers of cellulose, esters of cellulose, cellulose acetate, cellulose butyrates, cellulose propionate, ethyl cellulose mixed cellulose esters, etc), high molecular weight hydroxypropyl methylcellulose with a viscosity of a 2 wt. % aqueous solution of 3000-5600 cps or higher, acylated polysaccharides, polyurethanes, polyvinyl acetate (e.g., Kollicoat SR30D from BASF), polyacrylate and polymethacrylate polymers and derivatives, neutral copolymers comprising repeating units of ethyl acrylate and/or methylmethacrylate (such as Eudragit NE), pH-insensitive ammonio methacrylic acid copolymers, water-insoluble copolymers of acrylic and methacrylic acid esters with quaternary ammonium groups, such as Eudragit RS, RS30D, RL or RL30D and the like, and combinations thereof. The water-insoluble polymers in the ER coating compositions can be plasticized or unplasticized.

In another embodiment of the present invention, the ER coating composition comprises a water insoluble polymer and a plasticizer. Non-limiting examples of suitable plasticizers include glycerol and esters thereof (e.g., acetylated mono- or diglycerides including commercially available Myvacet® 9-45), glyceryl monostearate, glyceryl triacetate, glyceryl tributyrate, dibutyl phthalate, diethyl phthalate, dimethyl phthalate, dioctyl phthalate, acetylcitric acid tributyl ester, acetylcitric acid triethyl ester, tributyl citrate, acetyltributyl citrate, triethyl citrate, glyceroltributyrate; diethyl sebacate, dibutyl sebacate, dibutyl adipates, dibutyl azelates, dibutyl benzoates, chlorobutanol, polyethylene glycols, vegetable oils, diethyl fumarate, diethyl malates, diethyl oxalate, dibutyl succinate, dibutyl butyrate, cetyl alcohol esters, diethyl malonate, castor oils, polysorbates, N-butylbenzenesulfonamide, N-methylpyrrolidone, and mixtures thereof. The plasticizer may comprise about 3 to 30 wt. % (for example about 3 wt. %, about 5 wt. %, about 10 wt. %, about 15 wt. %, about 20 wt. %, about 25 wt. %, or about 30 wt. %) and more typically about 10 to 25 wt. % of the ER coating (relative to the amount of water-insoluble polymer).

The ER coating composition can be in the form of a solution (e.g., of the water-insoluble polymer and optional plasticizer in a suitable pharmaceutically acceptable solvent), or in the form of a dispersion (e.g., of the water-insoluble polymer and/or optional plasticizer in a suitable pharmaceutically acceptable liquid). In one embodiment, the ER coating composition comprises an aqueous dispersion of ethylcellulose and a plasticizer (e.g., dibutyl sebacate). In another embodiment, the ER coating composition comprises a solution of ethylcellulose (e.g., Ethocel Premium Standard 10 cps) and a plasticizer (e.g., diethyl phthalate) in acetone/water. In a further embodiment, the ER coating comprises a solution of ethylcellulose and diethyl phthalate in 98:2 acetone:water. In yet another embodiment, the ER coating contains about 90% ethylcellulose and about 10 wt. % diethyl phthalate. In still yet another embodiment, the ER coating composition comprises a solution of ethylcellulose and diethyl phthalate in a acetone:water mixture comprising about 85 wt % to 98 wt. % acetone and 15 wt. % to 2 wt. % water including weight ratios of acetone/water of about 88/12, about 90/10, about 92/8, and about 95/5 to about 98/2. In still a further embodiment, the ER coating composition comprises a solution of ethylcellulose and diethyl phthalate in about 98:2 acetone:water. In another embodiment, the ER coating composition comprises a solution of ethylcellulose in about 98:2 acetone.

The solids content of the ER coating composition can vary from about 5 wt. % to about 10 wt. %. In one embodiment, the solids content of the ER coating composition is about 6-7 wt. %. In yet another embodiment, the solids content of the ER coating composition is about 6.5 wt. %. In still another embodiment, the ER coating composition comprises a solution of ethylcellulose and diethyl phthalate in acetone/water, having about a 6 wt. % solids content.

The ER coating composition is prepared by stirring a mixture of a pharmaceutically acceptable water-insoluble polymer as described herein (e.g. ethylcellulose), optionally a plasticizer as described herein, and a pharmaceutically acceptable solvent (as described herein, e.g. an aqueous organic solvent). In one embodiment, the ER coating composition is prepared by stirring a mixture of a pharmaceutically acceptable water-insoluble polymer (e.g. ethylcellulose), a plasticizer (e.g. diethyl phthalate), and a pharmaceutically acceptable solvent (e.g. acetone/water), wherein the resulting solution is stirred after the addition of the plasticizer for up to 8 hours, but not less than one hour (e.g., for about 1-2 hours, for about 2-6 hours, for about 3-4 hours, or about 1 hour) to insure proper homogenization.

The ER composition coating step can be carried out, for example using a fluid bed coating apparatus at a spray rate of about 75-700 g/min, using a process air volume of 700-1500 CFM. The ER coated beads can be dried under suitable conditions, for example in the fluid bed coating apparatus under temperature and humidity conditions as described herein, for example at a product temperature of 27-40° C. (typically 33-34° C. at steady state) and dew point of about 5-20° C. (including about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., or about 20° C., inclusive of all values, ranges, and subranges therebetween; typically 10° C. at steady state).

If desired, after drying the ER beads can optionally be "sized" to remove fines (i.e., very fine particles) or agglomerates. For example the ER beads can be "sieved" with 14-mesh and 24-mesh screens to remove undersized and oversized particles.

Optionally, curing or further drying of the ER beads may be carried out, for example, in a conventional oven, more particularly in a tray-drying oven. Other drying or curing methods known in the art can also be used (e.g., drying under a gas stream). In one embodiment, the ER beads are dried at a dew point determined to give a desired drug release profile (e.g., after 2 hours, no more than about 40% of the total active is released; after 4 hours, from about 40-65% of the total active is released; after 8 hours, from about 60-85% of the total active is released; and optionally after 12 hours, from about 75-85% of the total active is released). In another embodiment, the ER beads are dried at a dew point of about 5-20° C. (including about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., or about 20° C., inclusive of all values, ranges, and subranges therebetween), for example about 6-17° C. or about 8-10° C. Any properly equipped drying apparatus can be used for drying under dew-point controlled conditions. For example, a conditioning unit that monitors and adjusts dew point can be added to the drying apparatus. Another suitable method involves using a drying gas dried using any drying/de-humidifying apparatus, where the drying gas is dried to the desired dew point.

A lower dew point correlates with drier air. Thus, alternatively, the drying process may be monitored and adjusted to maintain a desired relative humidity. In another embodiment, the ER beads are dried at a relative humidity determined to give a desired drug release profile (e.g., after 2 hours, no more than about 40% of the total active is released; after 4 hours, from about 40-65% of the total active is released; after 8 hours, from about 60-85% of the total active is released; and optionally after 12 hours, from about 75-85% of the total active is released). In another embodiment, the ER beads are dried at a relative humidity of about 0-20%, including about 2-10% and about 4-8% at atmospheric pressure.

In addition, drying or curing times and temperatures can be varied, so long as the conditions produce ER beads having a desired drug release profile. In one embodiment, the curing temperature is about 60° C.±5° C. Other curing temperatures such as about 5° C. 5° C. may also be employed. Likewise, curing times may vary, including, for example, up to 24 hours, about 2-24 hours, about 2-12 hours, about 2-6 hours, and about 4 hours. In one embodiment, the ER beads are cured at about 60° C. for about 4 hours. In another embodiment, the ER beads are cured while fluidizing at an inlet air temperature of about 60° C. for about 15 min in the fluid bed unit itself.

ER beads prepared as described above have a drug release profile, when tested using United States Pharmacopoeia Apparatus 2 (paddles @ 50 rpm) in 900 mL of 0.1 N HCl (or a suitable dissolution medium) at 37° C., substantially corresponding to the following pattern:

after 2 hours, no more than about 40% of the total active is released;

after 4 hours, from about 40-65% of the total active is released;

after 8 hours, from about 60-85% of the total active is released; and optionally after 12 hours, from about 75-85% of the total active is released.

When IR beads are coated with the ER coating composition under coating conditions (e.g., in a fluid bed coating apparatus) in which the temperature and humidity are maintained to provide a dew point of about 5-20° C., and optionally cured at a dew point of about 5-20° C. (e.g., 7-16° C.), the resulting ER beads show improved stability properties. For example, ER beads from commercial capsules, prepared in this manner and packaged in bottles subjected to long term stability test conditions (e.g., at 25% RH after storage for up to 48 months) consistently provide substantially uniform dissolution profiles when tested under in vitro conditions. In one embodiment, the ER beads thus prepared provide dissolution profiles where the drug concentration does not deviate by not more than 10% at any time point measured compared to the initial dissolution profile after about 3 months, 6 months, 12 months, 24 months, 36 months, or 48 months of storage. Extended release beads that are prepared using other processing conditions do not consistently exhibit comparable stability properties. For example, ER beads that are prepared by coating IR beads with an ER coating composition and optionally cured under conditions in which the dew point is not controlled, or under an atmosphere outside the dew point range of about 5-20° C. (e.g., 7-16° C.) do not consistently provide dissolution profiles that are stable throughout the expected duration of shelf-life (e.g., after 12 months, 24 months, 36 months, or up to 48 months storage in warehouses or pharmacies).

In addition, the uniformity of the release profile for ER beads in which the ER coating comprised a plasticizer was also found to depend on how the ER coating solution was prepared. In one embodiment, the ER coating is prepared by dissolving the water insoluble polymer (e.g., ethyl cellulose) in a suitable solvent (e.g., an aqueous organic solvent such as aqueous acetone), then adding the plasticizer to the solution and stirring the solution of water insoluble polymer and plasticizer for at least one hour after addition of the plasticizer. In some embodiments, the solution of water insoluble polymer and plasticizer is stirred for at least about 2 hours, at least about 3 hours, at least about 4 hours, at least about 5 hours after the addition of the plasticizer. If the water insoluble polymer and plasticizer solution is stirred for less than one hour after the addition of the plasticizer, the resulting ER beads do not consistently provide dissolution profiles that are stable over time (e.g., under storage conditions).

The cyclobenzaprine compositions prepared by the process of the present invention are useful for treating muscle spasms and the pain associated with muscle spasms, as well as fibromyalgia (a chronic syndrome characterized by diffuse or specific muscle, joint, or bone pain, fatigue, and other symptoms) and for the treatment of lower back pain.

The active core of the dosage form of the present invention may be comprised of an inert particle or an acidic or alkaline buffer crystal, which is coated with a drug-containing film-forming formulation and preferably a water-soluble film forming composition to form a water-soluble/dispersible particle. Alternatively, the active may be prepared by granulating and milling and/or by extrusion and spheronization of a polymer composition containing the drug substance. The amount of drug in the core will depend on the dose that is required, and typically varies from about 5 to 60 weight %. Generally, the polymeric coating on the active core will be from about 4 to 20% based on the weight of the coated particle, depending on the type of release profile required and/or the polymers and coating solvents chosen. Those skilled in the art will be able to select an appropriate amount of drug for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the drug to facilitate its release.

The drug-containing particle may be coated with an extended release (ER) coating comprising a water insoluble polymer or a combination of a water insoluble polymer and a water soluble polymer to provide ER beads. In accordance with certain embodiments, the water insoluble polymer and the water soluble polymer may be present at a weight ratio of from 100/0 to 65/35, more particularly from about 95/5 to 70/30, and still more particularly at a ratio of from about 85/15 to 75/25. The extended release coating is applied in an amount necessary to provide the desired release profile. The extended release coating typically comprises from about 1% to 15%, more particularly from about 7% to 12%, by weight of the coated beads.

The present invention also provides a method of making a modified release dosage form including a mixture of two bead populations. In accordance with one embodiment, the method includes the steps of:

preparing a drug-containing core by coating an inert particle such as a non-pareil seed, an acidic buffer crystal or an alkaline buffer crystal with a drug and a polymeric binder or by granulation and milling or by extrusion/spheronization to form an immediate release (IR) bead;

coating the IR bead with a water-insoluble polymer (optionally plasticized) alone (such as ethylcellulose) or in combination with a water soluble polymer (such as hydroxypropylmethylcellulose) to form an Extended Release (ER) bead;

filling into hard gelatin capsules ER Beads alone or in combination with IR Beads at a proper ratio to produce MR (modified release) capsules providing the desired release profile.

IR beads when tested in accordance with the following procedure release at least about 70%, more specifically at least about 90% of the active within 30 minutes.

Dissolution Procedure:

Dissolution Apparatus: USP Apparatus 2 (Paddles at 50 rpm), dissolution medium: 900 mL 0.1N HCl (or a suitable dissolution medium) at 37° C. and Drug Release determination by HPLC).

An aqueous or a pharmaceutically acceptable solvent medium may be used for preparing drug-containing core particles. The type of film forming binder that is used to bind the drug to the inert sugar sphere is not critical but usually water soluble, alcohol soluble or acetone/water soluble binders are used. Binders such as polyvinylpyrrolidone (PVP), polyethylene oxide, hydroxypropyl methylcellulose (HPMC), hydroxypropylcellulose (HPC), polysaccharides such as dextran, corn starch may be used at concentrations from about 0.5 to 5 weight %, although other concentrations may be useful. The drug substance may be present in this coating formulation in the solution form or may be dispersed at a solid content up to about 35 weight % depending on the viscosity of the coating formulation.

Examples of appropriate polymers for coating applications include waxes, water-insoluble cellulose derivatives (e.g. ethylcellulose, ethers of cellulose, esters of cellulose, cellulose acetate, cellulose butyrates, cellulose propionate, ethyl cellulose, mixed cellulose esters, etc), acylated polysaccharides, polyurethanes, polyvinyl acetate (e.g., Kollicoat SR30D from BASF), polyacrylate and polymethacrylate polymers and derivatives, neutral copolymers comprising repeating units of ethyl acrylate and/or methylmethacrylate (such as Eudragit NE), pH-insensitive ammonio methacrylic acid copolymers, water-insoluble copolymers of acrylic and methacrylic acid esters with quaternary ammonium groups, such as Eudragit RS, RS30D, RL or RL30D and the like, and combinations thereof. Preferred coating thicknesses range from about 1 to about 1000 microns, most preferably between about 20 to about 500 microns.

In accordance with certain embodiments, the drug substance, optionally a binder such as PVP, a dissolution rate controlling polymer (if used), and optionally other pharmaceutically acceptable excipients are blended together in a planetary mixer or a high shear granulator such as Fielder and granulated by adding/spraying a granulating fluid such as water or alcohol. The wet mass can be extruded and spheronized to produce spherical particles (beads) using an extruder/marumerizer. In these embodiments, the drug load could be as high as 90% by weight based on the total weight of the extruded/spheronized core.

Representative muscle relaxants include cyclobenzaprine, dantrolene sodium, methocarbamol, metaxalone, carisoprodol, diazepam and pharmaceutically acceptable salts, solvates, and/or esters thereof. Cyclobenzaprine hydrochloride is a particularly useful muscle relaxant. As used herein, the useful muscle relaxants include the base, pharmaceutically acceptable salts thereof such as hydrochloride, stereoisomers thereof and mixtures thereof.

Representative examples of water insoluble polymers useful in the ER coating include waxes, (e.g., fatty acid esters such as glyceryl behenate or caurnuba wax), ethylcellulose powder or an aqueous dispersion (such as AQUACOAT® ECD-30), cellulose acetate, polyvinyl acetate (Kollicoat SR#30D from BASF), neutral copolymers based on ethyl acrylate and methylmethacrylate (such as Eudragit NE), water-insoluble copolymers of acrylic and methacrylic acid esters with quaternary ammonium groups such as Eudragit RS and RS30D, RL or RL30D and the like. Representative examples of water soluble polymers useful herein include low molecular weight hydroxypropyl methylcellulose (HPMC), methylcellulose, hydroxypropylcellulose, polyvinylpyrrolidone, polyethylene glycol (PEG of molecular weight >3000) and mixtures thereof. The extended release coating will typically be applied at a thickness ranging from about 1 weight % up to 15 weight % depending on the solubility of the active in water and the solvent or latex suspension based coating formulation used.

The coating compositions used in forming the membranes are optionally plasticized. Representative examples of plasticizers that may be used to plasticize the membranes include triacetin, tributyl citrate, triethyl citrate, acetyl tri-n-butyl citrate diethyl phthalate, polyethylene glycol, polypropylene glycol, castor oil, dibutyl sebacate, acetylated monoglycerides, and the like or mixtures thereof. The plasticizer may comprise about 3 to 30 wt. % and more typically about 10 to 25 wt. % based on the polymer. The type of plasticizer and its content depends on the polymer or polymers, nature of the coating system (e.g., aqueous or solvent based, solution or dispersion based and the total solids).

In general, it is desirable to prime the surface of the particle before applying an extended release membrane coating or to separate the different membrane layers by applying a thin hydroxypropyl methylcellulose (HPMC) (OPADRY® Clear) film. While HPMC is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention is applied to multi-dose forms, i.e., drug products in the form of multi-particulate dosage forms (pellets, beads, granules or mini-tablets) or in other forms suitable for oral administration. As used herein, these terms are used interchangeably to refer to multi-particulate dosage forms.

The invention also provides a method of making an extended release dosage form which includes a mixture of two or more bead populations. In accordance with one aspect of the present invention, the method includes the steps of:

coating an inert particle such as a non-pareil seed, an acidic buffer crystal or an alkaline buffer crystal with a drug and polymeric binder to form an active drug particle (IR beads), which may be present in the unit dosage form to act as a bolus dose;

coating the active drug particle with a solution or suspension of a water insoluble polymer or a mixture of water soluble and water insoluble polymers to form an extended release coated drug particle (ER beads);

filling into a hard gelatin capsule ER beads alone and optionally, in combination with IR beads at a proper ratio ranging from 95/5 to 70/30 (ER beads/IR beads) to produce a MR (modified release) capsule exhibiting a target drug release profile.

The methods of the present invention provide a modified release, multi-particulate dosage form of a skeletal muscle relaxant comprising one or more bead populations which provides an extended release profile of the active under in vitro conditions closely mimicking the profile simulated from pharmaco-kinetic modeling. At least one of the bead populations is an ER (extended release) bead population typically comprising a coating of a water insoluble polymer alone, or in combination with a water soluble polymer, applied onto active containing cores. The active core of the dosage form of the present invention may comprise an inert particle such as a sugar sphere, or an acidic or alkaline buffer crystal, which is coated with a skeletal muscle relaxant such as cyclobenzaprine hydrochloride-containing film-forming formulation, preferably a water-soluble film forming composition. The first coating formulation may contain, in addition to the active, a binder such as hydroxypropyl cellulose. The drug layered beads may be coated with a protective seal coating of OPADRY® Clear to produce IR Beads. Alternatively, the core particle may be formed by granulating and dry milling and/or by extrusion and spheronization of a pharmaceutical composition containing the active. The amount of drug in the core will depend on the dose required and typically varies from about 5 to about 60% by weight.

ER Beads prepared by the methods of the present invention comprise a functional membrane (e.g., extended release membrane) comprising a water insoluble polymer alone or in combination with a water soluble polymer onto IR Beads.

The capsule formulation for once a day, oral administration of a skeletal muscle relaxant prepared in accordance with the present invention comprises ER Beads containing the active substance and optionally IR Beads. IR (immediate release) Beads allow immediate release of the active while ER Beads allow an extended release profile of the active over several hours. Upon oral administration, such a capsule formulation provides for therapeutically effective plasma profiles over an extended period of time, thereby resulting in improved patient compliance.

The dosage forms prepared by the methods of the present invention include one or more bead populations and provide a modified release profile. At least one of the bead populations includes extended release (ER) beads wherein the ER beads include a core particle (IR (immediate release) bead) containing a skeletal muscle relaxant and an ER (extended release) coating comprising a water insoluble polymer surrounding the core. The dosage form, in accordance with certain embodiments, when dissolution tested using United States Pharmacopoeia Apparatus 2 (paddles @ 50 rpm) in 900 mL of 0.1N HCl (or a suitable dissolution medium) at 37° C. exhibits a drug release profile substantially corresponding to the following pattern:

after 2 hours, no more than about 40% of the total active is released;

after 4 hours, from about 40-65% of the total active is released;

after 8 hours, from about 60-85% of the total active is released; and optionally after 12 hours, from about 75-85% of the total active is released.

The dosage form thereby provides a therapeutically effective plasma concentration over an extended period of time, typically over a period of 24 hours to treat muscle spasm associated with painful musculoskeletal conditions in humans. Alternatively, the dosage forms prepared by the methods of the present invention may be used to treat fibromyalgia or insomnia.

The following non-limiting examples illustrate the capsule dosage forms manufactured in accordance with the invention using cyclobenzaprine hydrochloride as a test case, which exhibit in vitro drug release profiles, similar to that predicted by performing modeling exercises. Such dosage forms when orally administered, would enable maintaining drug plasma concentrations at therapeutically effective levels over extended periods of time, thereby significantly improving patient compliance.

Example 1

Cyclobenzaprine is well absorbed after oral administration, but there is a large intersubject variation in plasma levels. It is eliminated quite slowly with a half-life as long as one to three days. The present treatment regimen of 10 mg three times daily is an issue of patient compliance, especially the elderly. Hence, a modified release dosage form (capsule) was designed with a release profile shown in FIG. 1. To determine if this is the proper release profile, the pharmacokinetics data of cyclobenzaprine following a single dose of 10 mg Flexeril® tablets administered 3 times a day was taken from the literature. A pharmacokinetic model was developed from this data using WinNonlin™ Version 1.5.

The resulting model parameters are listed below:

| Model Parameter | Value |
| --- | --- |
| Volume of Distribution/F | 429 L |
| K01 | 0.2031 hr$^{-1}$ |

-continued

| Model Parameter | Value |
| --- | --- |
| K10 | 0.1004 hr$^{-1}$ |
| K12 | 0.0828 hr$^{-1}$ |
| K21 | 0.0398 hr$^{-1}$ |
| Tlag | 0 hr |
| Dose | 2 × 10 mg Tablets |

Figure 2:
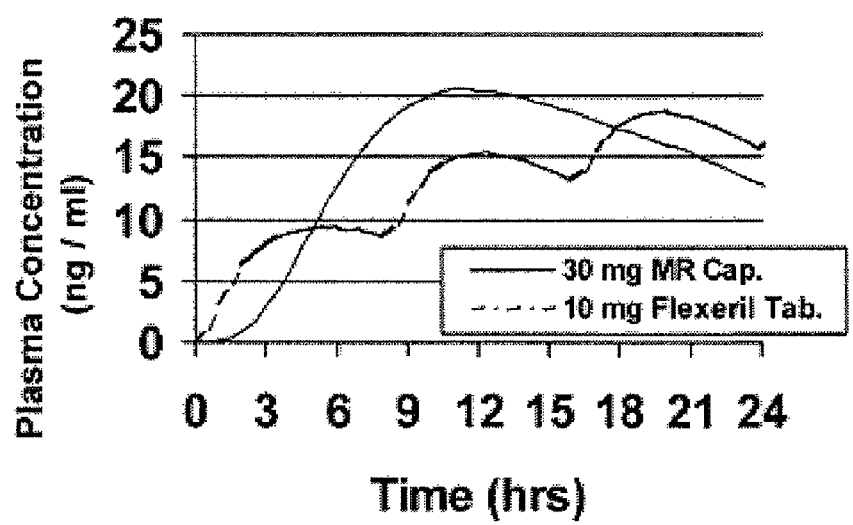
FIG. 2 shows the simulated Day 1 plasma level following dosing of 1×10 mg Flexeril® given 3 times a day and 1×30 mg cyclobenzaprine HCl MR capsule given once-daily.

Theoretical plasma levels were simulated using the pharmacokinetic model given above and the target in vitro release rate given in FIG. 1. FIG. 2 shows the simulated plasma levels for day one following dosing of 1×10 mg Flexeril® tablet given 3 times a day and the proposed Cyclobenzaprine HCl MR Capsule, 30 mg given once a day.

Example 2A

Figure 3:
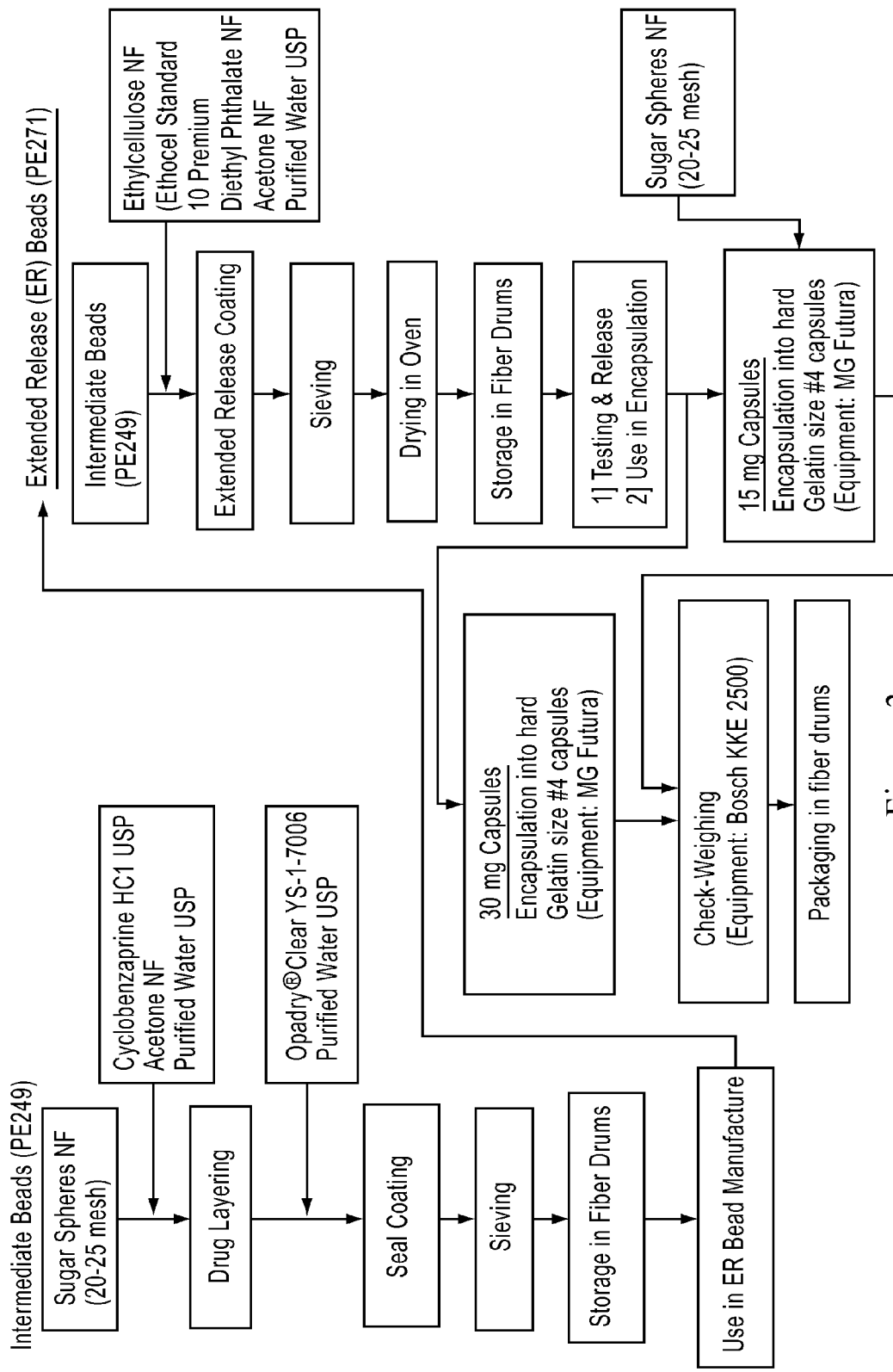
FIG. 3 shows a flow diagram of a cyclobenzaprine HCl MR capsule production process.

A manufacturing process flow diagram is shown in FIG. 3, used to prepare cyclobenzaprine HCl MR capsules. (See U.S. Pat. No. 7,387,793, herein incorporated by reference in its entirety for all purposes.) The capsules used for the various clinical studies (e.g., pivotal study and phased clinical trials) and the registration stability batches were also prepared according to the process of Example 2A.

A drug solution (25 wt. % solids) comprising cyclobenzaprine hydrochloride (20.0 kg) prepared in 50/50 acetone/purified water (30.0 kg each) and coated onto 20-25 mesh sugar spheres (58.4 kg) in a Glatt fluid bed coater, GPCG 120, equipped with a 18" bottom spray Wurster insert, air distribution plate D (100 mesh screen), a partition height from the distribution plate of about 53 mm, at the following conditions: Nozzle diameter: 3.0 mm; dew point about 8° C.; Atomization air pressure: 2 bar; Initial spray rate: 100 g/min ramping up to about 400 g/min; Product temperature: 49° C., decreasing to 43° C.; Process air volume: 950-1100 CFM. The resulting drug layered beads were provided with a protective seal coat of OPADRY® Clear at a coating level of 2 wt. % in the Glatt fluid bed coater by spraying the aqueous solution (8 wt. % solids) at a spray rate of about 200 g/min at a product temperature of 42° C. at a dew point of 8° C., then dried at about 50° C. for 5 minutes at a dew point of 8° C. to provide "immediate release" (IR) beads.

An ER coating composition (6.0 wt. % solids) comprising ethylcellulose (6.9 kg, Ethocel Premium Std, 10 cps) and diethyl phthalate (0.75 kg) in a 98/2 acetone/water solution was prepared by mixing at 850±25 rpm for not less than one hour. This means the time of mixing could be a variable at the discretion of the operator in the manufacturing environment. This coating composition was then applied onto the IR Beads (77.4 kg) under a dew point of 10° C. at an initial spray rate of about 250 g/min, ramping up to 500 g/min, process air volume of 1000 CFM), process air temperature 46° C., atomization air pressure 2.5 bar, in a Glatt GPCG 120, equipped with a 18" bottom spray Wurster insert, air distribution plate C (100 mesh screen), a partition height from the distribution plate of about 50 mm, nozzle port size 3 mm. The ER coating was applied at a dew point of 10° C. to provide a 9% coating weight. The resulting ER beads were dried in the unit at 50° C. for about 5 min at a dew point of 10° C. to drive-off residual solvents.

The ER beads were then passed through 14-mesh and 24-mesh screens, discarding any beads remaining on the 14 mesh screen, then cured in an oven at 60° C. for 4 hours. The required amounts of extended release beads (131.9 mg equivalent to 30 mg of cyclobenzaprine HCl) were then filled into size 4 capsules (empty capsule weight: 37 mg) to produce Cyclobenzaprine HCl MR Capsules, 30 mg as pivotal clinical trial material (CTM) using production-scale capsule filling equipment, MG Futura. The required amounts of extended release beads (65.9 mg equivalent to 15 mg of cyclobenzaprine HCl) and equivalent amounts of 20-25 mesh sugar spheres were also filled into size 4 white opaque capsules to produce Cyclobenzaprine HCl MR Capsules, 15 mg as pivotal CTM using the same capsule filler. Size 4 hard gelatin capsules with a body and cap colored differently and an identifying logo were employed for producing commercial products as Cyclobenzaprine HCl MR capsules, 15 & 30 mg.

Example 2B

A modified process was developed according to Example 2A with modifications to the ER coating and oven-curing steps. In the modified process, the IR beads were prepared as in Example 2A. In the ER coating step, the ER coating composition (prepared as in Example 2A) comprising ethylcellulose and diethyl phthalate in the acetone/water solution was prepared by mixing at 850±25 rpm for not less than 1 hr after the addition of diethyl phthalate. This coating composition was then applied onto the IR Beads at a dew point of 10° C. to provide a 9% coating weight. The resulting ER beads were dried in the unit at 50° C. for about 5 min at a dew point of 10° C. to drive-off residual solvents. After screening (14- and 24-mesh screens), the ER beads were cured in an oven at 60° C. for 4 hours at a dew point of 8-10° C. (target 10° C.).

Example 3

Figure 4:
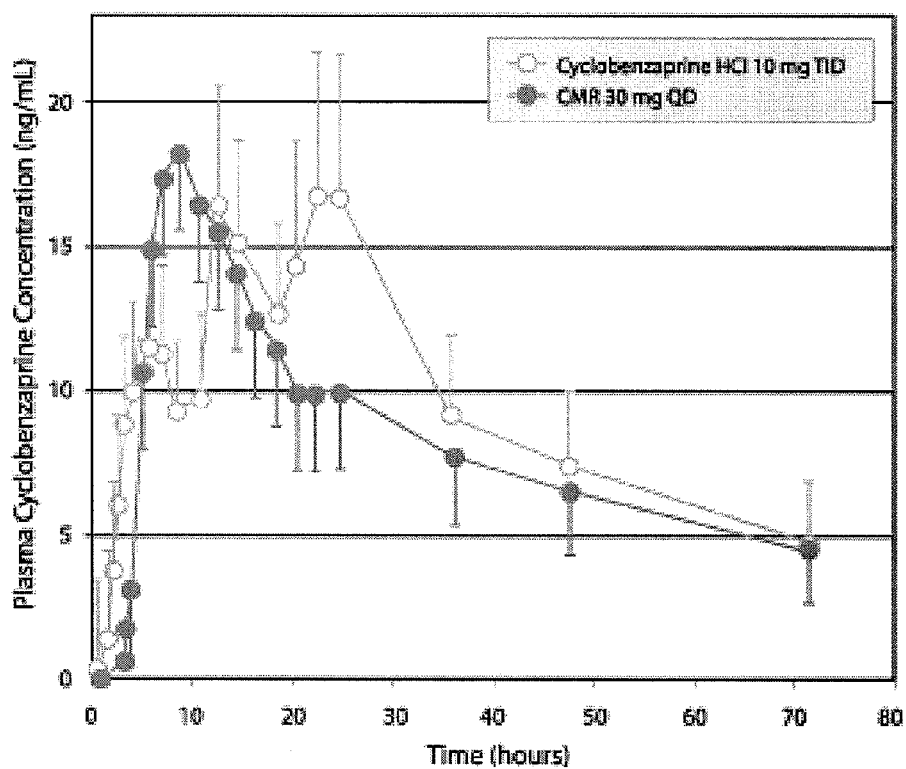
FIG. 4 shows the plasma concentration—time profiles of Cyclobenzaprine HCl modified-release (MR) capsules, 30 mg vs. Fexeril (Cyclobenzaprine HCl immediate-release (IR) tablets, 10 mg)×t.i.d. tested in pivotal PK clinical study.

Compositions prepared according to the procedure of Example 2A were tested in pharmacokinetic (PK) and Phase 3 clinical studies (fasted vs. fed state study using CMR 30 mg doses), safety and bioavailability study of multiple dosing of Cyclobenzaprine HCl MR 30 mg and Cyclobenzaprine HCl 10 mg three times daily in healthy volunteers, efficacy and safety study of Cyclobenzaprine HCl MR 15 mg and 30 mg vs. Placebo in subjects with pain due to muscle spasms of local origin, and a randomized, double-blind, two-period crossover trial in healthy volunteers (each 7-day assessment period). The latter trial compared the safety and pharmacokinetics of Cyclobenzaprine HCl Modified-Release (CMR) 30 mg once daily and Flexeril (cyclobenzaprine HCl 10 mg three times daily in two sub-groups of 18 healthy volunteers—aged 18 to 45 years and aged 65 to 75 years. Each 7-day assessment period consisted of blood collection and safety assessments at Predose, 0.5, 1, 1.5, 2, 2.5, 3, 4, 5, 6, 8, 10, 12, 14, 16, 18, 20, 22, 24, 36, 48, 72, 96, 120, 144, and 168 hrs after dosing and bioanalytical testing by validated LC-MS/MS. FIG. 4 shows the plasma concentration—time profiles of cyclobenzaprine HCl MR (CMR 30 mg) and Flexeril® (10 mg×3 times) administered into healthy adult volunteers fasted overnight.

TABLE 1A

Summary of target pharmacokinetic (PK) parameters in healthy adult subjects.

| Parameter Mean ± SD | CMR 15 mg | CMR 30 mg |
| --- | --- | --- |
| $AUC_{0-168}$ (ng · hr/mL) | 318.3 ± 114.7 | 736.6 ± 259.4 |
| $AUC_{0-\infty}$ (ng · hr/mL) | 354.1 ± 119.8 | 779.9 ± 277.6 |
| $C_{max}$ (mg/mL) | 8.3 ± 2.2 | 19.9 ± 5.9 |
| $T_{max}$ (hrs) | 8.1 ± 2.9 | 7.1 ± 1.6 |
| $T_{1/2}$ (hrs) | 33.4 ± 10.3 | 32.0 ± 10.1 |

Accordingly, one aspect of the invention relates to a process for preparing cyclobenzaprine HCl dosage forms for providing the pharmacokinetic (PK) parameters listed in Table 1A, obtained in the clinical studies described above, and, in another aspect, bioequivalent dosage forms, providing 80% to 125% of one or more of the mean pharmacokinetic parameters listed in Table 1A (e.g., $C_{max}$ and AUC). Each of the MR dosage forms containing cyclobenzaprine hydrochloride to be manufactured for commercial distribution following the regulatory approval, if tested in healthy volunteers, should provide a maximum blood plasma concentration ($C_{max}$) within the range of about 80% to 125% of 19.851±5.8765 ng/mL of cyclobenzaprine HCl and an $AUC_{0-168}$ within the range of about 80% to 125% of 736.60±259.414 ng·hr/mL following oral administration of a single 30 mg cyclobenzaprine HCl MR Capsule. Similarly, the cyclobenzaprine MR dosage forms should provide a maximum blood plasma concentration ($C_{max}$) within the range of about 80% to 125% of 8.315±2.1635 ng/mL of cyclobenzaprine HCl and an $AUC_{0-168}$ within the range of about 80% to 125% of 318.30±114.657 ng·hr/mL following oral administration of a single 15 mg cyclobenzaprine HCl MR Capsule.

Cyclobenzaprine HCl MR capsules of 30 mg were prepared according to Example 2A, providing within 80% to 125% of the mean pharmacokinetic values shown in Table 1B in healthy adult subjects aged 18-45 years under fasting conditions, and in Table 1C in healthy adult subjects aged 65-75 years under fasting conditions. $AUC_{0-168}$ refers to the area under the plasma concentration-time curve to the last measurable time point (168 hrs) calculated by the linear trapezoidal rule, $AUC_{0-\infty}$ refers to area under the concentration-time curve to infinity, $C_{max}$ refers to the maximum blood plasma concentration and $T_{max}$ refers to the time to maximum plasma levels of cyclobenzaprine. $C_{max(first)}$ and $T_{max(first)}$ values were estimated using plasma levels after the first dose and before second dose for cyclobenzaprine 10 mg TID, whereas for CMR 30 mg, the entire study period was used and the value was dose-adjusted to a 10-mg dose. $T_{max}$ was estimated using plasma levels during the entire study period for both study medications.

TABLE 1B

Mean (±SD) PK parameters for subjects 18 to 45 years of age in the Safety population

| Parameter | Flexeril ® 10 mg; tid (n = 17) | CMR 30 mg (n = 18) |
|---|---|---|
| $AUC_{0-168}$ (ng · hr/mL) | 805.4 ± 330.7 | 715.1 ± 264.2 |
| $AUC_{0-\infty}$ (ng · hr/mL) | 837.4 ± 340.2 | 751.2 ± 271.5 |
| $C_{max\,(first)}$ (ng/mL)[a] | 13.0 ± 4.6 | 6.4 ± 1.9 |
| $C_{max}$ (ng/mL)[b] | 18.1 ± 5.4 | 19.2 ± 5.6 |
| $T_{max\,(first)}$ (hrs)[a] | 4.3 ± 1.0 | 6.8 ± 1.9 |
| $T_{max}$ (hrs)[b] | 17.2 ± 5.7 | 6.8 ± 1.9 |
| $t_{1/2}$ (hrs) | 30.4 ± 7.1 | 32.4 ± 8.1 |

[a]Estimated using plasma levels after the first dose and before second dose for cyclobenzaprine 10 mg TID; for CMR 30 mg, the entire study period was used and the value was dose-adjusted to a 10-mg dose.
[b]Estimated using plasma levels during the entire study period for both study medications.

TABLE 1C

Mean (±SD) PK parameters for subjects 65 to 75 years of age in the Safety population

| Parameter | Flexeril ® 10 mg; tid (n = 17) | CMR 30 mg (n = 18) |
|---|---|---|
| $AUC_{0-168}$ (ng · hr/mL) | 1017.4 ± 261.3 | 945.9 ± 255.2 |
| $AUC_{0-\infty}$ (ng · hr/mL) | 1129.1 ± 309.6 | 1055.2 ± 301.9 |
| $C_{max\,(first)}$ (ng/mL) | 12.2 ± 2.6 | 6.4 ± 1.7 |
| $C_{max}$ (ng/mL) | 18.5 ± 3.3 | 19.2 ± 5.1 |
| $T_{max\,(first)}$ (hrs) | 5.0 ± 1.4 | 8.5 ± 2.3 |
| $T_{max}$ (hrs) | 19.7 ± 5.0 | 8.5 ± 2.3 |
| $t_{1/2}$ (hrs) | 47.1 ± 9.4 | 49.0 ± 8.3 |

Figure 5:
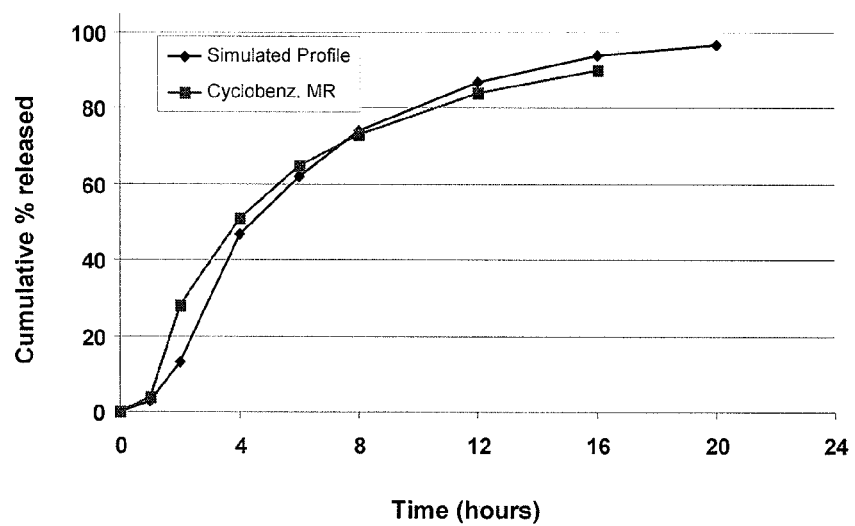
FIG. 5 shows the actual and simulated in-vitro release profiles for CMR 30 mg (simulated profile was obtained using the PK parameters derived from the clinical study.
Figure 6:
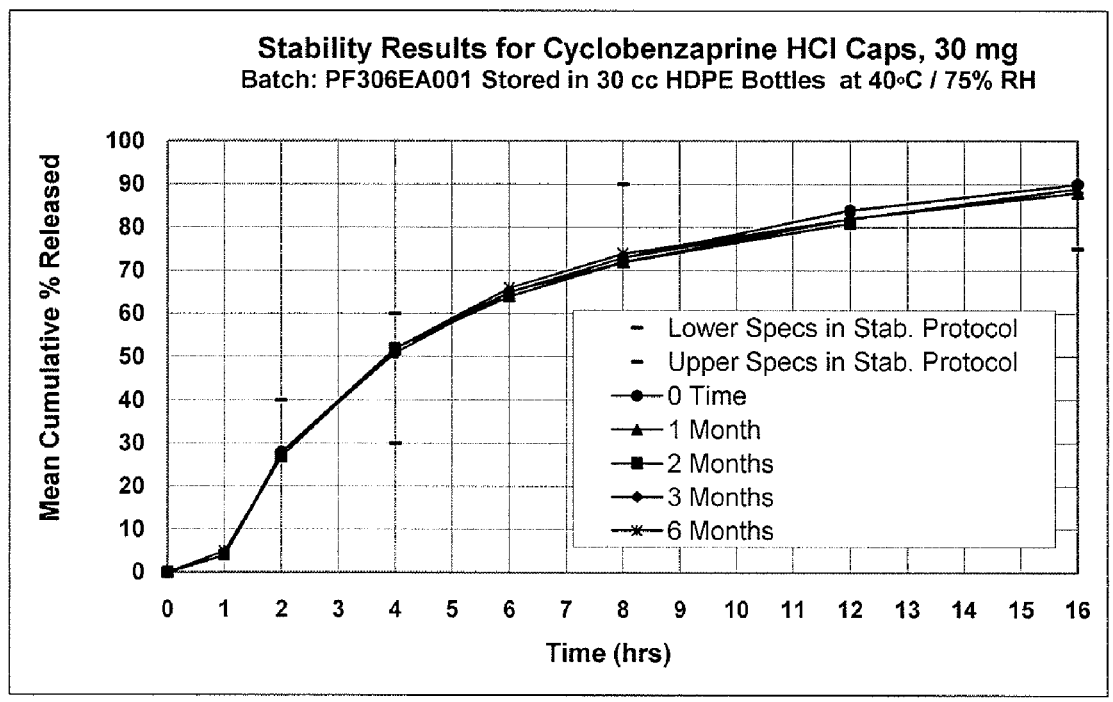
FIG. 6 shows the drug release profiles of Cyclobenzaprine HCl modified-release (MR) capsules, 30 mg stored in induction-sealed HDPE bottles at 40° C./75% RH

FIG. 5 shows the actual in vitro drug release profile in comparison to the simulated in vitro drug release profile calculated using the Gastro-Plus software and the PK parameters obtained from the studies described above. The two profiles are remarkably very close. FIG. 6 shows the drug release profiles of the pivotal biobatch (30 mg, prepared according to Example 2A) stored in 60-ct induction-sealed HDPE bottles under accelerated stability conditions (40 C/75% RH (relative humidity)). 15 mg (PF307EA001) and all Registration stability batches (PF312 (15 mg) and PF313 (30 mg), also prepared according to Example 2A) exhibited similarly tight drug release profiles when stored in 60-ct induction-sealed HDPE bottles under ICH stability conditions (e.g., at 25° C./60% RH for 36 months, 30° C./65% RH for 12 months, and 40° C./75% RH for 6 months).

Example 4

Table 2 summarizes the stability results for a series of process validation batches of Cylcobenzaprine HCl MR capsules, 15 and 30 mg (e.g., PF312EA001V to PF312EA003V (15 mg) and PF313EA001V to PF313EA003V, prepared according to Example 2A). The first validation batch (PF313EA001) and another batch (PF313EA006) had comparatively high and low dissolutions at release (i.e., at time zero), respectively (see Table 3). Lot# PF3130001V failed for dissolution at 1-, 3-, and 6-month 40° C./75% RH (relative humidity), 3-, 6-month 25° C./60% RH and 3 month at 30° C./65% RH time points. The out-of-specification dissolution points were the 4 hour and/or 8 hour time points. The other five validation batches at release (i.e., at time zero) met dissolution, assay, degradant specifications (see Table 2). Furthermore, the stability data for these validation batches also met the product specifications. The investigation indicated the out-of-specification (OOS) dissolution results observed for PF3130001V were not due to a stability issue with the product but rather a higher than typical dissolution profile for this particular lot at release (i.e., at time zero). The time zero and subsequent time dissolution data did not indicate an upward trend in the dissolution values but rather typical analytical and/or batch-to-batch variability.

TABLE 2

Analytical Data for Cyclobenzaprine HCl MR Capsules, 15 & 30 mg (Process Validation Batches)

| Cyclobenzaprine HCl MR Capsule | Assay (%) | Moisture (%) | % Drug Released | | | | Total % Impurity |
|---|---|---|---|---|---|---|---|
| | | | 2 hrs | 4 hrs | 8 hrs | 16 hrs | |
| Cyclobenzaprine HCl MR Capsules, 30 mg Validation Batch PF3130001V in HDPE Bottle | | | | | | | |
| Initial | 100.1 | 2.1 | 36 (34-38) | 60 (57-62) | 80 (76-83) | 93 (88-96) | 0.0 |
| 25° C./60% RH, 3 mo | 100.3 | 1.6 | 36 (34-37) | 62 (60-65) | 82 (79-86) | 97 (95-101) | 0.2 |
| 25° C./60% RH, 6 mo | 99.9 | 2.1 | 37 (36-39) | 63 (58-67) | 84 (77-88) | 99 (94-103) | 0.1 |
| 25° C./60% RH, 12 mo | 101.2 | 2.7 | 33 (31-34) | 58 (56-59) | 76 (74-78) | 89 (87-92) | 0.2 |

TABLE 2-continued

Analytical Data for Cyclobenzaprine HCl MR Capsules, 15 & 30 mg
(Process Validation Batches)

| Cyclobenzaprine HCl MR Capsule | Assay (%) | Moisture (%) | % Drug Released | | | | Total % Impurity |
|---|---|---|---|---|---|---|---|
| | | | 2 hrs | 4 hrs | 8 hrs | 16 hrs | |
| 40° C./75% RH, 1 mo | 100.0 | 2.3 | 36 (35-38) | 61 (59-64) | 82 (78-87) | 93 (90-97) | 0.1 |
| 40° C./75% RH, 3 mo | 99.0 | 2.2 | 35 (33-38) | 62 (59-65) | 83 (79-85) | 97 (94-101) | 0.2 |
| 40° C./75% RH, 6 mo | 100.3 | 2.0 | 34 (33-36) | 63 (60-65) | 84 (80-87) | 98 (95-99) | 0.2 |
| Cyclobenzaprine HCl MR Capsules, 30 mg Validation Batch PF3130002V in HDPE Bottle | | | | | | | |
| Initial | 99.7 | 1.9 | 31 (30-33) | 56 (54-58) | 75 (73-78) | 88 (86-92) | 0.0 |
| 25° C./60% RH, 3 mo | 98.9 | 2.0 | 32 (30-33) | 59 (56-61) | 80 (76-83) | 97 (93-100) | 0.1 |
| 25° C./60% RH, 6 mo | 98.7 | 1.5 | 30 (28-32) | 56 (54-59) | 77 (74-80) | 93 (89-95) | 0.2 |
| 25° C./60% RH, 12 mo | 101.5 | 1.8 | 31 (28-32) | 56 (54-57) | 74 (71-75) | 88 (85-89) | 0.0 |
| 25° C./60% RH, 18 mo | 101.2 | 2.0 | 29 (27-30) | 54 (51-56) | 73 (69-76) | 87 (82-92) | 0.1 |
| 40° C./75% RH, 1 mo | 100.3 | 2.4 | 31 (30-31) | 58 (56-59) | 78 (76-79) | 93 (90-96) | 0.2 |
| 40° C./75% RH, 3 mo | 98.3 | 2.1 | 31 (30-32) | 58 (57-59) | 79 (78-80) | 94 (93-97) | 0.1 |
| 40° C./75% RH, 6 mo | 100.8 | 1.5 | 29 (28-29) | 56 (55-57) | 76 (74-79) | 91 (89-93) | 0.3 |
| Cyclobenzaprine HCl MR Capsules, 30 mg Validation Batch PF3130003V in HDPE Bottle | | | | | | | |
| Initial | 98.0 | 2.3 | 31 (30-32) | 56 (54-58) | 76 (73-78) | 90 (88-93) | 0.0 |
| 25° C./60% RH, 3 mo | 98.0 | 2.0 | 32 (30-34) | 58 (56-60) | 78 (76-80) | 91 (89-93) | 0.1 |
| 25° C./60% RH, 6 mo | 97.9 | 1.9 | 33 (30-34) | 57 (52-62) | 77 (72-82) | 94 (90-97) | 0.2 |
| 25° C./60% RH, 12 mo | 98.7 | 2.3 | 30 (29-30) | 55 (53-56) | 74 (73-75) | 88 (86-90) | 0.3 |
| 25° C./60% RH, 18 mo | 98.7 | 1.9 | 29 (27-31) | 54 (52-56) | 73 (69-75) | 87 (82-90) | 0.1 |
| 40° C./75% RH, 1 mo | 98.5 | 2.0 | 32 (30-34) | 57 (54-60) | 77 (73-80) | 90 (86-94) | 0.3 |
| 40° C./75% RH, 3 mo | 96.6 | 2.2 | 30 (28-31) | 57 (54-59) | 78 (74-81) | 92 (87-95) | 0.1 |
| 40° C./75% RH, 6 mo | 98.9 | 1.3 | 29 (27-30) | 57 (54-59) | 80 (74-83) | 93 (88-96) | 0.2 |
| Cyclobenzaprine HCl MR Capsules, 15 mg Validation Batch PF3120001V in HDPE Bottles | | | | | | | |
| Initial | 98.4 | 2.6 | 24 (22-26) | 50 (48-51) | 71 (65-74) | 87 (78-91) | 0.0 |
| 25° C./60% RH, 3 mo | 96.2 | 1.9 | 26 (21-29) | 53 (48-56) | 74 (69-79) | 90 (86-94) | 0.1 |
| 25° C./60% RH, 6 mo | 96.5 | 1.7 | 28 (22-31) | 55 (50-58) | 77 (73-79) | 92 (89-95) | 0.2 |
| 25° C./60% RH, 12 mo | 97.2 | 2.4 | 23 (22-26) | 50 (48-52) | 71 (67-74) | 87 (80-91) | 0.2 |
| 25° C./60% RH, 18 mo | 96.0 | 2.0 | 22 (20-25) | 49 (46-52) | 71 (67-73) | 85 (81-88) | 0.1 |
| 40° C./75% RH, 1 mo | 97.3 | 2.5 | 24 (23-28) | 51 (49-54) | 72 (69-74) | 88 (84-90) | 0.1 |
| 40° C./75% RH, 3 mo | 95.6 | 2.3 | 24 (20-27) | 53 (47-60) | 75 (70-80) | 91 (86-93) | 0.1 |
| 40° C./75% RH, 6 mo | 98.3 | 1.9 | 22 (17-29) | 51 (49-56) | 74 (71-79) | 90 (86-96) | 0.2 |
| Cyclobenzaprine HCl MR Capsules, 15 mg Validation Batch PF3120002V in HDPE Bottles | | | | | | | |
| Initial | 99.6 | 2.4 | 23 (21-27) | 50 (47-54) | 72 (69-75) | 88 (86-91) | 0.0 |
| 25° C./60% RH, 3 mo | 100.7 | 2.1 | 24 (22-26) | 53 (49-54) | 75 (70-76) | 91 (85-92) | 0.1 |
| 25° C./60% RH, 6 mo | 98.4 | 1.8 | 26 (22-29) | 55 (46-59) | 75 (69-82) | 94 (91-97) | 0.1 |
| 25° C./60% RH, 12 mo | 99.8 | 2.1 | 24 (22-25) | 52 (49-55) | 73 (70-76) | 87 (84-92) | 0.2 |
| 25° C./60% RH, 18 mo | 99.2 | 2.0 | 22 (17-28) | 51 (45-56) | 73 (69-78) | 93 (88-99) | 0.1 |
| 40° C./75% RH, 1 mo | 99.2 | 2.4 | 22 (19-24) | 50 (47-54) | 72 (69-76) | 89 (85-94) | 0.1 |
| 40° C./75% RH, 3 mo | 98.9 | 2.3 | 27 (25-28) | 54 (52-56) | 76 (72-80) | 92 (87-97) | 0.1 |
| 40° C./75% RH, 6 mo | 99.9 | 2.0 | 23 (20-25) | 54 (52-58) | 75 (71-81) | 88 (84-90) | 0.1 |
| Cyclobenzaprine HCl MR Capsules, 15 mg Validation Batch PF3120003V in PVC Blisters | | | | | | | |
| Initial | 96.3 | 2.1 | 24 (21-27) | 52 (50-53) | 73 (71-75) | 88 (85-91) | 0.0 |
| 25° C./60% RH, 3 mo | 98.6 | 2.2 | 22 (19-25) | 49 (47-51) | 71 (68-73) | 87 (83-89) | 0.0 |
| 25° C./60% RH, 6 mo | 98.2 | 1.9 | 20 (17-23) | 48 (45-51) | 70 (68-71) | 85 (83-88) | 0.0 |
| 25° C./60% RH, 12 mo | 97.8 | 2.9 | 24 (21-25) | 49 (46-50) | 68 (65-71) | 83 (78-87) | 0.1 |
| 25° C./60% RH, 18 mo | 98.2 | 2.3 | 20 (17-22) | 47 (43-51) | 68 (64-72) | 83 (80-87) | 0.0 |
| 40° C./75% RH, 1 mo | 99.7 | 3.0 | 24 (22-26) | 53 (50-57) | 76 (74-81) | 92 (89-99) | 0.1 |
| 40° C./75% RH, 3 mo | 98.6 | 2.3 | 24 (22-25) | 51 (47-53) | 74 (71-76) | 90 (87-92) | 0.1 |
| 40° C./75% RH, 6 mo | 99.2 | 2.5 | 24 (23-24) | 50 (48-52) | 72 (69-76) | 88 (83-92) | 0.0 |

Two modifications were made to the process of Example 2A. First, the stirring time after addition of plasticizer in the ER coating solution was consistently controlled to be at least one hour with an upper limit of, for example, 2 hrs. Second, a desiccant wheel was installed to tightly control the dew point during drying/curing. A target dew point for drug layering, ER bead coating, and ER bead curing was set at 8-10° C.

Table 3 summarizes the mean values with standard deviations, maximum and minimum values of assay, dissolutions, moisture, total degradants, and uniformity of dosage units for the commercial batches after the new controls were consistently adopted (i.e., stirring time and curing dew point control of Example 2B): 7 batches of cyclobenzaprine HCl MR capsules, 30 mg (PF313) and 32 batches of cyclobenzaprine HCl MR capsules, 15 mg (PF312). The earlier Process Validation Batch PF3130001V and one of the first 3 commercial batches (PF3130006) referred to above (manufactured according to Example 2A) which showed atypical (i.e., high or low) dissolution values, are shown separately in Table 3. It is apparent that the assay and dissolution values are tight, indicating that the manufacturing processes are sufficiently robust.

TABLE 3

Analytical Data for 15 & 30 mg Cyclobenzaprine HCl MR Capsules

| Cyclobenzaprine HCl MR Capsules | Assay Mean (%) | Moisture (%) | % Drug Released | | | | Total Impurity (%) | Uniformity of Dosage Units | |
|---|---|---|---|---|---|---|---|---|---|
| | | | 2 hrs | 4 hrs | 8 hrs | 16 hrs | | Assay (%) | Mean Stdev |
| Validation Batch (PF3130001V) and Commercial Batch (PF3130006) of Cyclobenzaprine HCl MR Capsules, 30 mg, with Atypical Drug Release Profiles | | | | | | | | | |
| PF313EA001V | 101.3 | 1.7 | 35 | 60 | 79 | 93 | 0.03 | 100.0 | 4.1 |
| PF313EA006 | 100.7 | 1.0 | 20 | 46 | 67 | 84 | 0.00 | 101.1 | 5.8 |
| Mean of 7 Batches of Cyclobenzaprine HCl MR Capsules 30 mg (PF313) | | | | | | | | | |
| Mean | 100.4 | 1.54 | 30.3 | 55.7 | 75.2 | 89.3 | 0.07 | 100.9 | 2.55 |
| Stdev | 0.96 | 0.18 | 3.0 | 3.5 | 3.8 | 3.5 | 0.04 | 1.49 | 0.56 |
| Max (%) | 101.9 | 1.9 | 35 | 61 | 80 | 93 | 0.11 | 103.7 | 3.25 |
| Min (%) | 99.3 | 1.4 | 26 | 51 | 69 | 84 | 0.02 | 99.4 | 1.69 |
| Mean of 32 Batches of Cyclobenzaprine HCl MR Capsules 15 mg (PF312) | | | | | | | | | |
| Mean | 99.6 | 2.1 | 24.1 | 50.5 | 71.2 | 86.7 | 0.066 | 99.8 | 3.38 |
| Stdev | 2.72 | 0.52 | 3.40 | 3.64 | 3.76 | 3.54 | 0.049 | 2.88 | 1.03 |
| Max (%) | 103.9 | 3.0 | 33 | 58 | 79 | 93 | 0.20 | 106.3 | 5.81 |
| Min (%) | 92.2 | 1.0 | 17 | 43 | 63 | 79 | 0.00 | 94.7 | 1.74 |

While the invention has been described in detail and with reference to specific examples thereof, it will be apparent to one skilled in the art that various changes and modifications can be made without departing from the spirit and scope thereof.

We claim:

1. A method of preparing a pharmaceutical composition comprising:
    a) coating inert particles with a drug layering composition comprising cyclobenzaprine or a pharmaceutically acceptable salt, solvate, and/or ester thereof, and a pharmaceutically acceptable solvent, thereby forming IR beads;
    b) coating the IR beads with an ER coating composition comprising a pharmaceutically acceptable water-insoluble polymer, under an atmosphere having a dew point ranging from about 5-20° C., thereby forming ER beads; and
    c. curing the ER beads at about 60° C. for about 4-12 hours under an atmosphere having a dew point ranging from about 5-20° C.

2. The method of claim 1, further comprising coating the IR beads of step a) with a seal-coating composition comprising a pharmaceutically acceptable water-soluble polymer before said ER coating step b).

3. The method of claim 2, wherein said inert particles have a particle size of about 20-25 mesh.

4. The method of claim 2, wherein said seal-coating composition further comprises water.

5. The method of claim 1, wherein said coating steps a) and b) are carried out under an atmosphere having a dew point ranging from about 5-20° C.

6. The method of claim 1, wherein the ER coating composition further comprises a plasticizer.

7. The method of claim 6, wherein the ER coating composition is prepared by stirring the pharmaceutically acceptable water-insoluble polymer, plasticizer, and pharmaceutically acceptable solvent for at least about 1 hour after addition of the plasticizer to the pharmaceutically acceptable water-insoluble polymer and pharmaceutically acceptable solvent.

8. The method of claim 7, wherein the pharmaceutically acceptable water-insoluble polymer, plasticizer, and pharmaceutically acceptable solvent are stirred for at least about 3 hours after addition of the plasticizer to the pharmaceutically acceptable water-insoluble polymer and pharmaceutically acceptable solvent.

9. The method of claim 1, wherein the drug layering composition further comprises cyclobenzaprine hydrochloride and about 50:50 acetone:water.

10. The method of claim 2, wherein the pharmaceutically acceptable water-soluble polymer comprises hydroxypropyl methylcellulose.

11. The method of claim 1, wherein the pharmaceutically acceptable water-insoluble polymer is selected from the group consisting of ethylcellulose, ethers of cellulose, esters of cellulose, cellulose acetate, cellulose butyrate, cellulose propionate, polyvinyl acetate, neutral copolymers based on ethyl acrylate and methyl methacrylate, copolymers of acrylic and methacrylic acid esters with quaternary ammonium groups, pH-insensitive ammonio methacrylic acid copolymers, waxes, acetylated polysaccharides, polyurethanes, high molecular weight hydroxypropyl methylcellulose, polyacrylate and polymethacrylate polymers, and mixtures thereof.

12. The method of claim 1, wherein the pharmaceutically acceptable water-insoluble polymer comprises ethylcellulose.

13. The method of claim 6, wherein the plasticizer is selected from the group consisting of diethyl phthalate, triacetin, tributyl citrate, tri-ethyl citrate, acetyl tri-n-butyl citrate, dibutyl sebacate, polyethylene glycol, polypropylene glycol, castor oil, acetylated mono- and di-glycerides, glyceryl monostearate, glyceryl triacetate, glyceryl tributyrate, phthalates, citrates, glyceroltributyrate; sebacates, adipates, azelates, benzoates, chlorobutanol, polyethylene glycols, vegetable oils, olive oil, castor oil, mineral oil, fumarates, malates, oxalates, succinates, butyrates, cetyl alcohol esters, malonates, polysorbates, glycerine, N-butylbenzenesulfonamide, N-methylpyrrolidone, and mixtures thereof.

14. The method of claim 6, wherein the plasticizer comprises diethyl phthalate.

15. The method of claim 6, wherein the ER coating composition comprises ethylcellulose and diethyl phthalate dissolved in a solvent comprising acetone and water at a acetone/water weight ratio ranging from about 85/15 to about 98/2.

16. The method of claim 6, wherein the ratio of water-insoluble polymer to plasticizer is about 9:1.

17. The method of claim 1, wherein the drug layering composition comprises cyclobenzaprine hydrochloride, and after drying, the drug layered beads comprise from about 20 wt. % to about 30 wt. % cyclobenzaprine hydrochloride.

18. The method of claim 17, wherein the drug layering composition comprises cyclobenzaprine hydrochloride, and after drying, the drug layered beads comprise about 25 wt. % cyclobenzaprine hydrochloride.

19. The method of claim 2, wherein the IR beads comprise about 2% of the pharmaceutically acceptable water soluble polymer.

20. The method of claim 1, wherein the ER beads comprise about 7% to about 12% of the pharmaceutically acceptable water insoluble polymer.

21. The method of claim 6, wherein the ER beads comprise about 9% of the pharmaceutically acceptable water-insoluble polymer and plasticizer.

22. The method of claim 1, wherein the ER beads provide a drug release profile that does not deviate by more than about 10% at any time point in the following dissolution pattern:
  after 2 hours, no more than about 40% of the total active is released;
  after 4 hours, from about 40-65% of the total active is released;
  after 8 hours, from about 60-85% of the total active is released; and
  optionally after 12 hours, from about 75-85% of the total active is released,
when tested using United States Pharmacopoeia Apparatus 2 (paddles @ 50 rpm) in 900 mL of 0.1 N HCl at 37° C.

23. The method of claim 1, wherein the ER beads provide a drug release of about 20% to about 50% after 2 hours when tested using United States Pharmacopoeia Apparatus 2 (paddles @ 50 rpm) in 900 mL of 0.1 N HCl at 37° C.

24. The method of claim 1, wherein said coating step b) is carried out under an atmosphere having a dew point ranging from about 6-17° C.

25. The method of claim 1, wherein said curing step c) is carried out under an atmosphere having a dew point ranging from about 6-17° C.

26. The method of claim 1, wherein said coating step a) is carried out under an atmosphere having a dew point ranging from about 6-17° C.

27. The method of claim 1, wherein the pharmaceutical composition comprises 30 mg of cyclobenzaprine HCl and provides a maximum blood plasma concentration ($C_{max}$) within the range of about 80% to 125% of about 19.9 ng/mL of cyclobenzaprine HCl and an $AUC_{0-168}$ within the range of about 80% to 125% of about 736.6 ng·hr/mL following a single oral administration thereof.

28. The method of claim 1, wherein the pharmaceutical composition comprises 15 mg of cyclobenzaprine HCl and provides a maximum blood plasma concentration ($C_{max}$) within the range of about 80% to 125% of about 8.3 ng/mL of cyclobenzaprine HCl and an $AUC_{0-168}$ within the range of about 80% to 125% of about 318.3 ng·hr/mL following a single oral administration thereof.

* * * * *